United States Patent [19]

Giuffre et al.

[11] 4,285,876

[45] Aug. 25, 1981

[54] ISOCYANATE ADDUCTS WITH β-DIKETONES

[75] Inventors: Luigi Giuffre, Milan, Italy; Placido M. Spaziante, Lugano, Switzerland

[73] Assignee: Vertac, Inc., Memphis, Tenn.

[21] Appl. No.: 83,399

[22] Filed: Oct. 10, 1979

[51] Int. Cl.³ ............... C07C 119/042; C07C 125/063
[52] U.S. Cl. ............ 260/453 SP; 260/453 P; 260/453 AL; 560/157; 560/163
[58] Field of Search ...... 260/453 P, 453 AL, 453 SP; 560/157, 162

[56] References Cited

U.S. PATENT DOCUMENTS

| | | | |
|---|---|---|---|
| 3,074,998 | 1/1963 | Whetstone et al. | 560/157 |
| 3,625,993 | 12/1971 | Horn | 560/157 X |
| 4,003,938 | 1/1977 | Roenig et al. | 260/453 P |
| 4,082,787 | 4/1978 | Bassett et al. | 260/453 P |
| 4,123,450 | 10/1978 | Weber, Jr. | 260/453 P |
| 4,138,422 | 2/1979 | Chan et al. | 560/157 X |
| 4,146,550 | 3/1979 | Reichmann et al. | 260/453 P |

*Primary Examiner*—Dolph H. Torrence
*Attorney, Agent, or Firm*—Hammond & Littell, Weissenberger and Muserlian

[57] ABSTRACT

Adducts of low boiling isocyanates with β-diketones which decompose on heating to give the low boiling isocyanates as a condensible vapor; as well as the method of making the adducts and the method of storing and transporting low boiling isocyanates employing said adducts.

13 Claims, No Drawings

ISOCYANATE ADDUCTS WITH β-DIKETONES

BACKGROUND OF THE INVENTION

Methyl isocyanate, ethyl isocyanate and other low boiling isocyanates are difficult to store and transport due to their high vapor pressure, toxicity and flammability. Even such compounds as phenyl isocyanate and the isomeric tolyl isocyanates which boil at temperatures from 167° C. to about 200° C. present storage and transportation problems.

Many compounds are known to react with isocyanates through double bond addition to the N=C bond. Reaction with alcohols form N-methylcarbamoyl esters which are relatively stable compounds. The reaction of naphthyl isocyanate with phenols is a classic method of characterizing phenols.

It has been conventional to obtain low boiling isocyanates from the corresponding carbamoyl chloride by heating in an appropriate solvent while separating the hydrochloric acid from the gaseous isocyanate. A recent U.S. Pat. No. 4,082,787 makes a review of various processes.

U.S. Pat. No. 4,003,938 describes a method for obtaining low boiling isocyanates by decomposing the corresponding β-naphthyl carbamates at temperatures of from 150° C. to 500° C. This process, however, presents difficulties as the β-naphthyl carbamate is a solid at room temperature and the reaction requires a vacuum.

The low boiling isocyanates are alkyl isocyanates having from 1 to 10 carbon atoms, preferably from 1 to 4 carbon atoms, in the alkyl and alkenyl isocyanates having from 2 to 6 carbon atoms in the alkenyl. Such compounds have the boiling points given in Table I.

TABLE I

| Isocyanate | Boiling Point °C. |
| --- | --- |
| Methyl | 38–45 |
| Ethyl | 60 |
| Isopropyl | 74 |
| n-Propyl | 88 |
| Allyl | 88 |
| n-Butyl | 115 |
| t.-Butyl | 85 |
| CH₃—C(CH₃)₂—CH(CH₃)— | 58 (13 mm) |
| di-(n-propyl) methyl | 40 (12 mm) |

U.S. Pat. No. 4,146,550 describes a process for preparation of aliphatic monoisocyanates by reacting the corresponding carbamic acid chloride with sulfuric acid or sulfonic acid amides, certain activated phenols containing electrophilic groups and certain substituted urethanes and then subjecting the reaction product to pyrolysis at temperatures of from 100° C. to 250° C. to recover the aliphatic isocyanates. This process requires the use of a solvent such as chlorobenzene, and the aliphatic isocyanates and solvent are recovered as a mixture which must be carefully redistilled to recover the aliphatic isocyanate.

U.S. Pat. No. 3,074,998 describes various carbamates esters of enols of the formula

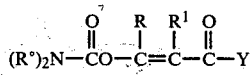

including 1-methyl-3-oxo-1-butenyl N-dimethyl-carbamate. No utility is given for this compound although compounds where Y is H, OR or —N(R°)₂ are disclosed as having insecticidal, herbicidal and fungicidal properties. Patentee's other examples all relate to N-dimethyl carbamates which have Y equal to H, OR, —N(R°)₂ or CN.

U.S. Pat. No. 4,138,422 describes reactions of isocyanates with active hydrogen compounds, including aliphatic alcohols such as isopropanol, in the presence of solid particulate matter as catalyst to give N-mono-substituted-carbamates.

U.S. Pat. No. 3,625,993 describes the reaction of alkylamines with phosgene in a heated reactor followed by passage of the gases through an active hydrogen compound such as aliphatic alcohols, particularly methanol to decanol, in liquid form where the corresponding alkyl carbamate ester is formed and unreacted starting materials and hydrogen chloride pass off as gases.

U.S. Pat. No. 2,903,478 describes the reaction of α-naphthol with phosgene to give the chloroformate, which is reacted with an alkylamine to give the α-naphthyl N-alkyl carbamate.

OBJECTS OF THE INVENTION

An object of the present invention is to develop an adduct of low boiling isocyanates which form liquids or solids which readily undergo a reversible reaction on heating to release the low boiling isocyanate as a gas.

Another object of the present invention is to obtain an adduct of (1) an isocyanate having the formula

wherein R is a member selected from the group consisting of alkyl having from 1 to 10 carbon atoms and alkenyl having 2 to 6 carbon atoms with a β-diketone selected from the group consisting of compounds having the formula

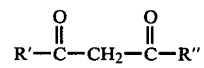

wherein R' is lower alkyl and R" is a member selected from the group consisting of lower alkyl, alkoxy, phenyl and, when taken together lower alkylene having 2 to 6 carbon atoms, and decalin-1,8-dione.

A further object of the present invention is the development of a process for storing and transporting an isocyanate having the formula

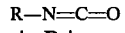

wherein R is a member selected from the group consisting of alkyl having from 1 to 10 carbon atoms and alkenyl having from 2 to 6 carbon atoms, consisting of the steps of (1) reacting said isocyanate with a β-diketone selected from the group consisting of compounds having the formula

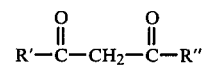

wherein R' is lower alkyl and R" is a member selected from the group consisting of lower alkyl, alkoxy, phenyl and when taken together, lower alkylene having 2 to 6 carbon atoms, and decalin-1,8-dione, or reacting said β-diketone with phosgene and reacting the chloroformate ester produced with an amine having the formula

R—NH$_2$ wherein R has the above assigned values, or reacting a carbamoyl chloride having the formula $$R-NH-\overset{\overset{O}{\|}}{C}-Cl$$

with said β-diketone, to form an adduct with or without evolution of HCl gas, (2) maintaining said adduct at temperatures below the decomposition temperature for the time desired, and (3) heating said adduct to decompose the same with evolution of the isocyanate as a vapor.

These and other objects of the invention will become more apparent as the description thereof proceeds.

DESCRIPTION OF THE INVENTION

The above objects have been accomplished by the present discovery of adducts of low boiling isocyanates with β-diketones which decompose on heating to give the low boiling isocyanates as a condensible vapor; as well as the method of making the adducts and the method of storing and transporting low boiling isocyanates employing said adducts.

In addition, the present invention relates to a process for storing and transporting an isocyanate having the formula:

R—N=C=O wherein R is a member selected from the group consisting of alkyl having from 1 to 10 carbon atoms and alkenyl having from 2 to 6 carbon atoms, consisting of the steps of (1) reacting said isocyanate with a β-diketone selected from the group consisting of compounds having the formula $$R'-\overset{\overset{O}{\|}}{C}-CH_2-\overset{\overset{O}{\|}}{C}-R''$$

wherein R' is lower alkyl and R" is a member selected from the group consisting of lower alkyl, alkoxy, phenyl, and when taken together, lower alkylene having 3 to 6 carbon atoms, and decalin-1,8-dione, or reacting said β-diketone with phosgene and reacting the chloroformate ester produced with an amine having the formula

R—NH$_2$ wherein R has the above-assigned values, or reacting a carbamoyl chloride having the formula $$R-NH-\overset{\overset{O}{\|}}{C}-Cl$$

with said β-diketone, to form an adduct with or without evolution of HCl gas, (2) maintaining said adduct at temperatures below the decomposition temperature for the time desired, and (3) heating said adduct to decompose the same with evolution of the isocyanate as a vapor. This vapor can be condensed if desired to recover the isocyanate. In some cases it may be desirable to further utilize the isocyanate as a vapor. The β-diketone remaining can be recycled to form further adduct.

The β-diketones have been found to be excellent carriers for low boiling isocyanates, particularly those of the formula

R—N=C=O wherein R is a member selected from the group consisting of alkyl having from 1 to 10, preferably from 1 to 4, carbon atoms and alkenyl having from 2 to 6, preferably 3 to 4, carbon atoms, such as methyl isocyanate (MIC), boiling at 38° C. to 45° C., depending on purity, ethyl isocyanate, n-propyl isocyanate, isopropyl isocyanate, n-butyl isocyanate, isobutyl isocyanate, t-butyl isocyanate, 2-methylbutyl isocyanate, pentyl isocyanate, neopentyl isocyanate, n-hexyl isocyanate, 1-methyl-2,2-dimethyl-propyl isocyanate, 1-propyl-butyl isocyanate, n-octylisocyanate, n-decyl isocyanate, vinyl isocyanate, allyl isocyanate, isopropenyl isocyanate, 1,1-dimethyl-allyl isocyanate, etc. The preferred isocyanate employed, due to its use in organic synthesis, is methyl isocyanate.

As is well known, β-diketones exist in equilibrium between a keto and an enol from, but predominately in the enol form

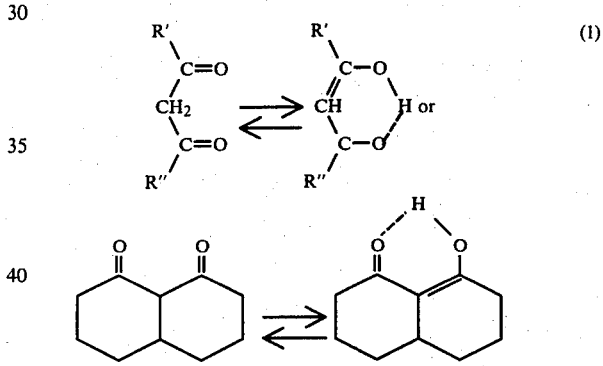

This equilibrium can be shifted to the right in the presence of a base, such as triethylamine, or of any compound which reacts with the enol form. When an isocyanate is employed, an acid catalyst increases the cationic activity of the isocyanate. The reaction with an isocyanate follows the course of reaction (2)

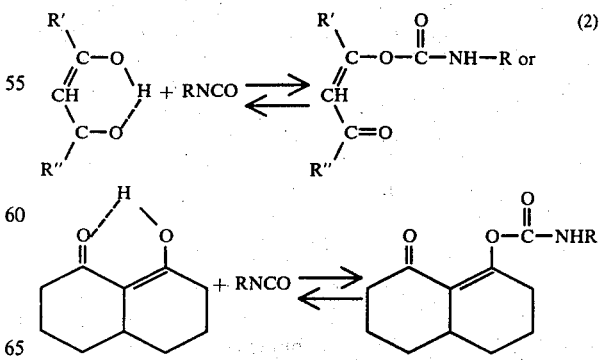

Preferably the above reaction is conducted in the presence of catalytic amounts of a tertiary amine with maintenance of the reaction temperature between 25° C. and 100° C.

When phosgene is employed, the reaction is thought to follow the course of reaction (3)

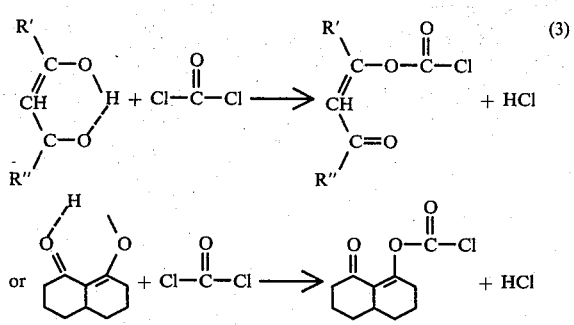

The chloroformate is then reacted with an amine according to reaction (4)

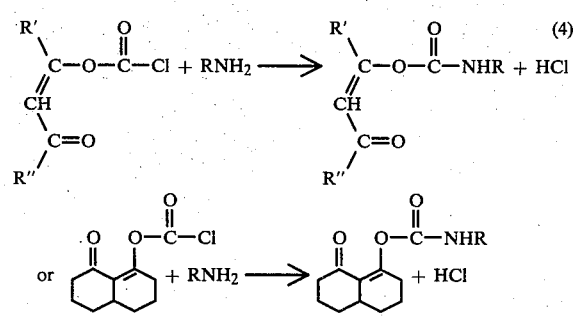

When a carbamoyl chloride is employed, the reaction follows the course of reaction (5)

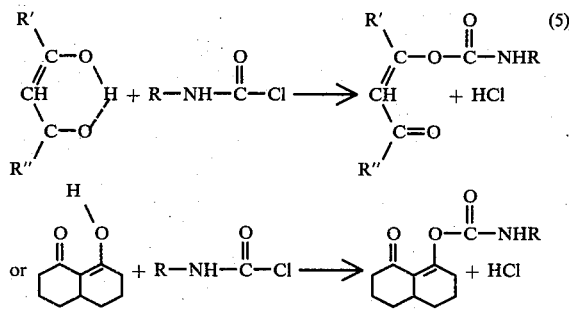

Again no catalyst is required in the presence of the evolved HCl. In the above reactions (3), (4) and (5) the temperature is maintained at elevated temperatures, such as between 25° C. and 100° C.

The N-mono-substituted carbamate can be subsequently decomposed into the initial β-diketone and the isocyanate $$R-N=C=O$$

at an elevated temperature.

The reactions (2) or (3) and (4) or (5) are conducted at temperatures where said β-diketone is in the liquid phase. The reactions can be conducted in stoichiometric amounts although an excess of β-diketone is often desirable as a solvent. Preferably the β-diketone is employed in amounts of from 1 to 100 times the stoichiometric amount.

The β-diketones of the formula

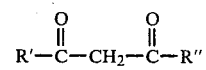

are compounds having boiling points of well above 100° C., such as acetylacetone, benzoylacetone, methyl acetoacetate, cyclohexane-1,3-dione cyclopentane-1,3-dione, decalin-1,8-dione, etc.

It is also part of the present invention to employ freshly prepared isocyanate or carbamoyl chloride from the reaction of phosgene with an amine according to the reactions:

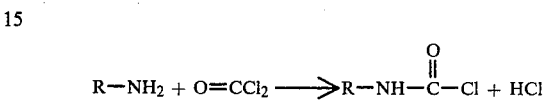

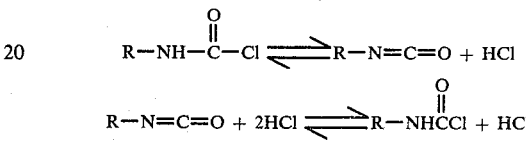

Each of the above reactions are equilibrium reactions and at higher temperatures the production of R—N=C=O is encouraged.

The gaseous reactants phosgene and the low boiling amine are mixed at elevated temperatures and then immediately contacted with the liquid β-diketones whereby the adduct is formed and HCl vapors pass off. The β-diketone may also be present in a solvent. Preferably, the temperature of the β-diketone is maintained above its freezing point and both below the adduct decomposition temperature and the boiling point of the β-diketone, such as in the range of 25° C. and 100° C.

The above reactions are ordinarily conducted with an excess of the β-diketone acting as a solvent, although stoichiometric amounts are also employed. An organic solvent can also be utilized which is inert to the isocyanate or carbamoyl chloride. This solvent should have basic properties according to the Lewis theory, such as lower alkyl ethers, dioxane, sulfolane, tetrahydrofuran, etc.

The adducts of the isocyanate with the β-diketones will decompose when heated to give a gaseous isocyanate and the liquid β-diketone. It is thus possible to form the adduct, store the same at a temperature below the decomposition temperature and ship the same to the consumer. The consumer then heats the adduct to liberate the gaseous isocyanate which is then processed as desired. The carrier β-diketone, or its solution, can thus be recovered and returned for reuse to produce more adduct.

At any temperature, the adduct exists in an equilibrium with its constituents; however, the amount of isocyanate and β-diketone present in the equilibrium mixture is barely detectable at temperatures below the decomposition temperature of the particular adduct. The decomposition temperature for any particular adduct can be readily determined experimentally.

Preferably, the adduct is heated to substantially higher temperatures than the decomposition temperature, but below the decomposition temperature for the β-diketone component thereof. When temperatures of from 100° C. to 250° C. are employed, from 70% to 75% of the low-boiling isocyanate can be recovered. However, at temperatures of over 160° C., with an adduct of methyl isocyanate and acetylacetone, both the methyl isocyanate and acetylacetone are gases and unless carefully separated, considerable adduct formation occurs when the acetylacetone condenses. The remainder of the adduct present together with the β-diketone can be recycled to form further adduct.

The following examples are illustrative of the practice of the invention without being limitative in any respect.

EXAMPLE 1

Production of the adduct of methyl isocyanate with acetylacetone 25 cc (0.2427 mols) of acetylacetone (AA) and 0.13 cc of triethylamine were charged into a jacketed reactor equipped with a reflux condenser, thermometer and magnetic stirrer. The reaction temperature was kept constant by means of a thermostated circulating fluid bath.

The condenser temperature was kept at 2° C. to 3° C. by circulating iced water. The top end of the condenser carries a silica-gel tube to keep moisture from condensing into the reactor.

7.50 cc (0.1213 mols) of methyl isocyanate (MIC) were charged to give a mol ratio MIC:AA of 1:2. The amount of triethylamine catalyst present was about 1 mol % per mol of MIC. The reaction mass was heated and kept at 40° C. for 3 hours and 30 minutes with the cooling time to 16° C. for sampling excluded. During the reaction samples at 16° C. were taken at the following times:

0, 30 min., 1 hour and 30 min., 3 hours and 30 min., diluted (1 to 10) with sym.-dichloroethane and analyzed by infra-red spectroscopy. The presence of methyl isocyanate is evidenced by a band at 2280 cm$^{-1}$. The sample taken at 3 hours and 30 minutes showed an almost complete elimination of the band at 2280 cm$^{-1}$, whereas bands at 3440, 1745 and 1540$^{cm-1}$ increase.

At the end of the reaction, the solution turned a deep yellow. The product is a solution of 1-methyl-3-keto-1-butenyl N-methylcarbamate in acetylacetone.

EXAMPLE 2

The reactor described in Example 1 was employed but the run was conducted as follows.

AA = 50 cc. (0.4854 mols)
MIC = 15 cc. (0.2427 mols)
Et$_3$N = 0.3 cc.

The mol ratio of MIC to AA was 1:2.

Four reactions were run at different temperatures of 50° C., 60° C., 70° C. and 80° C. for 1 hour. Samples were taken at 0 time and 1 hour as in Example 1 and analyzed by infra-red spectroscopy.

The spectra demonstrated that the MIC 2280 cm$^{-1}$ band disappeared after 1 hour at 70° C. and also at 80° C. The bands at 3440, 1745 and 1570 cm$^{-1}$ increased with time. The spectra after 1 hour at 60° C. still shows a slight band at 2280 cm$^{-1}$.

This example demonstrates the dependance of the reaction on temperature.

EXAMPLE 3

The reactor described in Example 1 was employed but the run was conducted as follows. 'AA = 50 cc. (0.4854 mols)
MIC = 30 cc. (0.4854 mols)
Et$_3$N = 0.7 cc. (0.005 mols)

The mol ratio of MIC to AA was 1:1.

The reaction temperature was maintained at 70° C. for 30 minutes; after this time the temperature rose to 93° showing that the reaction is exothermic. The solution turned from yellow to deep red. The temperature was then controlled at 80° for 2.5 hours.

The IR spectrum taken after the reaction was completed showed that the MIC 2280 cm$^{-1}$ band and the 1700 cm$^{-1}$ AA band were absent while the 3440, 1745, 1560 cm$^{-1}$ bands were strong.

EXAMPLE 4

Release of Methyl Isocyanate

The adduct from Example 2, run at 70° C., was slowly heated in a reactor equipped with a thermometer, a capillary ending tube to bubble nitrogen through the reaction mass, a jacketed Vigreux column with thermometer ending with a Claisen distillation head, a condenser and a tube to bubble the condensate in a jacketed graduated cylinder.

The decomposition reactor is heated with an oil bath. The Vigreux column is kept around 36° to 40° C. and the graduated cylinder for collection for the condensate distilling from the reaction mass is kept at 16° C. through circulation of running water.

This cylinder contains an absorbing solution of n-butylamine in dioxane. The volume and the titer of the butylamine solution is known. The absorption of methyl isocyanate by the amine occurs as follows:

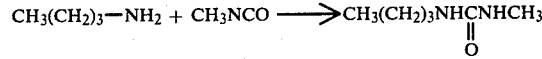

The reaction progress is followed by taking samples at different times and titrating the residual amine with HCl. No interference in this titration from the reaction product n-butyl-N′-methyl urea occurs. The reacted butylamine is equivalent to the amount of MIC formed during the decomposition reaction.

In this run an aliquot of the reaction mass from the Example 2, run at 70° C., in which the MIC/AA ratio was ½ was used.

The volume of the mass employed was equivalent to about 56 mmols of MIC (which is the theoretical amount to be obtained free after the decomposition). The reaction was run at temperatures of 100° C., 120° C. and 140° C. for 1 hour. 100 ml of 1N butylamine having been used. Three samples, 10 ml each, were taken and titrated potentiometrically with N/2 HCl. The results are summarized below:

| T° C. | 100° C. | 120° C. | 140° C. |
|---|---|---|---|
| Obtained MIC mmols | 3.03 | 4.09 | 7.05 |
| Total MIC obtained | 14.17 mmols | | |

The theoretical MIC present is 56 mmols. The decomposition yield is therefore 25%.

EXAMPLE 5

Release of Methyl Isocyanate

The procedure of Example 4 was followed however, in this run, the product of Example 3 was employed. The MIC/AA ratio was 1/1 . 15 ml of the product of Example 3 equivalent to 91 mmols of MIC were used.

The reaction was carried out at 140° C. to 150° C. for 2 hours.

120 ml of butylamine 1N solution were used. In the developed analysis 10 ml of butylamine solution were taken and titrated with N/2 HCl.

| Obtained MIC | 30.25 mmols | |
|---|---|---|
| Initial AA bound MIC | 91 mmols | |
| Yield | $\frac{30.25}{91.10} \cdot 10^2 = 33.25\%$ | |

EXAMPLE 6

Release of Methyl Isocyanate

The procedure of Example 4 was followed, however, in this run, the product of Example 3 was employed. The MIC/AA ratio was 1/1. The product of Example 3 was added dropwise within 30 minutes in the reactor kept at 160° C., 10 ml of the reaction mass equivalent to 60.6 mmols of MIC were used and kept at 160° C. for 30 minutes after the addition was completed.

| Obtained MIC | 24.745 mmols | |
|---|---|---|
| Initial AA bound MIC | 60.6 mmols | |
| Yield | $\frac{24.745}{60.6} \cdot 10^2 = 40.83\%$ | |

At 160° C., both the MIC and AA are gases and considerable adduct formation occurs when the AA condenses in the presence of gaseous MIC. This can be avoided and the yields of MIC increased by separation of the two gases or by slow condensation of the AA.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the production of the adduct of an isocyanate having the formula $$R-N=C=O$$

wherein R is a member selected from the group consisting of alkyl having from 1 to 10 carbon atoms and alkenyl having 2 to 6 carbon atoms with a β-diketone selected from the group consisting of compounds having the formula $$R'-\overset{O}{\underset{\|}{C}}-CH_2-\overset{O}{\underset{\|}{C}}-R''$$

wherein R' is lower alkyl and R'' is a member selected from the group consisting of lower alkyl, alkoxy, phenyl and when taken together, lower alkylene having 2 to 6 carbon atoms, and decalin-1,8-dione, consisting essentially of the steps of reacting said isocyanate with a β-diketone selected from the group consisting of compounds having the formula $$R'-\overset{O}{\underset{\|}{C}}-CH_2-\overset{O}{\underset{\|}{C}}-R''$$

wherein R' is lower alkyl and R'' is a member selected from the group consisting of lower alkyl, alkoxy, phenyl and when taken together, lower alkylene having 2 to 6 carbon atoms, and decalin-1,8-dione, in a molar ratio of 1:1 to a molar excess of β-diketone at a temperature between 25° C. and 100° C., to form said adduct.

2. The process of claim 1 wherein said reaction is conducted in the presence of catalytic amounts of a catalyst selected from the group consisting of a tertiary amine and an inorganic acid.

3. The process of claim 1 wherein R is methyl.

4. The process of claim 1 wherein said isocyanate is methyl isocyanate and said β-diketone is acetylacetone.

5. The process of claim 1 wherein said reaction is conducted in the presence of an organic solvent having basic properties according to Lewis theory.

6. A process for storing and transporting an isocyanate having the formula $$R-N=C=O$$

wherein R is a member selected from the group consisting of alkyl having from 1 to 10 carbon atoms and alkenyl having from 2 to 6 carbon atoms, consisting of the steps of (1) reacting said isocyanate with a β-diketone selected from the group consisting of compounds having the formula $$R'-\overset{O}{\underset{\|}{C}}-CH_2-\overset{O}{\underset{\|}{C}}-R''$$

wherein R' is lower alkyl and R'' is a member selected from the group consisting of lower alkyl, alkoxy, phenyl and when taken together, lower alkylene having 2 to 6 carbon atoms, and decalin-1,8-dione, or reacting a carbamoyl chloride having the formula $$R-NH-\overset{O}{\underset{\|}{C}}-Cl$$

with said β-diketone, to form an adduct, (2) maintaining said adduct at temperatures below the decomposition temperature for the time desired, and (3) heating said adduct to decompose the same with evolution of the isocyanate.

7. The process of claim 6 wherein said isocyanate is reacted with said β-diketone in a molar ratio of 1:1 to a molar excess of β-diketone at a temperature between 25° C. and 100° C.

8. The process of claim 7 wherein said reaction is conducted in the presence of a catalyst selected from the group consisting of a tertiary amine and an inorganic acid.

9. The process of claim 7 wherein R is methyl.

10. The process of claim 7 wherein said isocyanate is methyl isocyanate and said β-diketone is acetylacetone.

11. The process of claim 7 wherein said reaction is conducted in the presence of an organic solvent having basic properties according to Lewis theory.

12. The process of claim 6 wherein said heating step to decompose said adduct is conducted at a temperature of from 100° C. to 500° C.

13. The process of claim 12 wherein said heating step is conducted at a temperature of from 120° C. to 160° C.

* * * * *